United States Patent [19]

Eikeland et al.

[11] Patent Number: 5,772,728
[45] Date of Patent: *Jun. 30, 1998

[54] METHOD FOR UPGRADING OF SILICON-CONTAINING RESIDUES OBTAINED AFTER LEACHING OF COPPER-CONTAINING RESIDUES FROM CHLOROSILANE SYNTHESIS

[75] Inventors: Inger Johanne Eikeland, Oslo; Roald Gundersen, Vennesla; Ragnhild Jensen, Kristiansand, all of Norway

[73] Assignee: Elkem ASA, Norway

[ * ] Notice: The term of this patent shall not extend beyond the expiration date of Pat. No. 5,651,807.

[21] Appl. No.: 859,819

[22] Filed: May 19, 1997

Related U.S. Application Data

[63] Continuation of Ser. No. 537,934, Oct. 26, 1995, abandoned.

[30] Foreign Application Priority Data

Mar. 30, 1994 [NO] Norway .................................. 941174

[51] Int. Cl.⁶ .................................................. C01B 33/00
[52] U.S. Cl. ........................... 75/430; 75/10.5; 75/10.51; 420/578; 420/117
[58] Field of Search ................................ 75/10.5, 10.51; 420/578, 117

[56] References Cited

U.S. PATENT DOCUMENTS

| | | | |
|---|---|---|---|
| 3,704,114 | 11/1972 | Wilson et al. | 75/3 |
| 3,768,998 | 10/1973 | Yonemochi | 75/12 |
| 4,758,352 | 7/1988 | Feldner et al. | 210/719 |
| 5,174,810 | 12/1992 | Dosaj et al. | 75/10.61 |
| 5,651,807 | 7/1997 | Gundersen et al. | 75/10.48 |

FOREIGN PATENT DOCUMENTS

| | | | |
|---|---|---|---|
| 0141125 | 5/1985 | European Pat. Off. | C01B 33/02 |
| 0287934 | 10/1988 | European Pat. Off. | C01B 33/02 |
| 0901889 | 1/1954 | Germany . | |
| 3201312 | 7/1983 | Germany | C01B 33/02 |
| 3523541 | 1/1987 | Germany | C01G 3/02 |
| 4205980 | 9/1993 | Germany | C07F 7/16 |

*Primary Examiner*—David A. Simmons
*Assistant Examiner*—M. Alexandra Elve
*Attorney, Agent, or Firm*—Bierman, Muserlian and Lucas

[57] ABSTRACT

The present invention relates to a method for upgrading silicon-containing solid residues obtained after leaching of copper from copper-containing residues from direct synthesis of organochlorosilanes. Solid residue, optionally together with an oxidation agent, is supplied to a smelting furnace where the residues are melted and form a molten metallic phase substantially containing silicon and a calcium silicate slag and tapping of the molten metallic phase and an inert slag from the smelting furnace.

8 Claims, No Drawings

METHOD FOR UPGRADING OF SILICON-CONTAINING RESIDUES OBTAINED AFTER LEACHING OF COPPER-CONTAINING RESIDUES FROM CHLOROSILANE SYNTHESIS

This application is a continuation of application Ser. No. 08/537,934 filed Oct. 26, 1995 now abandoned.

TECHNICAL FIELD

The present invention relates to a method for upgrading residues from methylchlorosilane synthesis, where silicon is reacted with methylchloride in the presence of a copper catalyst and residues from chlorosilanesynthesis, where silicon is reacted with hydrogenchloride.

BACKGROUND ART

Methylchlorosilane synthesis, also called direct synthesis, is carried out in fluidized bed reactors. During the process a part of fine particulate silicon and copper catalyst particles are together with metallic compounds, especially iron- and aluminium compounds, which are present in the silicon raw material, removed from the reactor together with the gaseous reaction products, a mixture of silanes, and unreacted methylchloride. The solid materials are separated from the mixture of silanes and unreacted methylchloride in separating devices such as for example cyclones. In addition a residue will remain in the reactor, comprising silicon, copper and metal halides formed from compounds in the silicon raw materials and also comprising carbon deposits formed by decomposition of methylchloride. This residue is continuously or intermittently removed from the reactor.

Elemental copper, copper oxides, copper formate, copper hydroxides and other copper salts like copper chloride are used as a copper catalyst. The copper catalyst may further contain metals or metal compounds as activators, such as zinc, and zinc compounds, or promotors such as antimony, cadmium, phosphorus, tin, arsenic etc. in order to improve the reactivity and the selectivity of the produced silanes.

These residues have up till now normally been deposited on waste disposal sites. However, as the residues normally contain 1–10% by weight of copper, mainly in elemental form, copper may be leached from the residue which represents a danger for pollution of ground water. It is therefore no longer acceptable to deposit this type of residue on disposal sites.

A number of methods for recovering copper from the above mentioned residues have been proposed. Thus from German patent No. 901889 it is known to treat residue from the reactor in water and diluted hydrochloric acid under addition of chlorine gas in order to leach copper as divalent copper chloride and remove the remaining solid residue from the solution whereafter divalent copper chloride in the leach solution is reduced to cuprous chloride which is crystallized and used as a copper catalyst in the direct synthesis. The remaining solid residue, which mainly contains silicon must, however, be deposited. In addition it is difficult to obtain a complete crystallization of cuprous chloride from the leach solution, making it necessary to subject the final solution to further treatment.

From DE-A1 3523541 it is known a method for treatment of a hydrolysis residue from organosilane production, where the residue is oxidized by sodium hypochlorite in order to leach copper from the residue. After removal of the solids from the leach solution, an alkaline earth- or alkaline hydroxide or an alkaline carbonate are added in order to precipitate copper oxides, hydroxides or carbonates. Also in this process the undissolved solid material which mainly contains silicon, is deposited.

In U.S. Pat. No. 4,758,352 it is proposed to oxidize hydrolysis residue by using an oxygen containing gas. Also in this process only copper is recovered, while a silicon containing residue is deposited.

In DE-A 4205980 it is proposed to treat residue from direct synthesis by diluted sulphuric acid at elevated temperatures in order to dissolve copper and where copper can be precipitated as for example cuprous chloride or as copper-II-oxalat or where copper can be recovered by electrolysis. It is further disclosed in DE-A 4205980 that it is obtained a solid silicon residue which can be used in metallurgical processes or which can be deposited. Chemical analysis of the obtained silicon residue is, however, not given.

By all the above-mentioned processes the residues are subjected to a leaching process in order to dissolve and recover copper while the undissolved solid matter is normally deposited. This undissolved matter does, however, contain a substantial amount of silicon which is not recovered.

DISCLOSURE OF INVENTION

It is an object of the present invention to provide a method for upgrading silicon-containing solid residues obtained after leaching of copper from copper-containing residues from direct synthesis of organochlorosilanes, whereby a silicon-containing product can be recovered and whereby an inert slag can be produced and can be used as a filler material and can be deposited without restrictions. By an inert slag it is understood a material which satisfies the requirements set to an inert material in Review of Regulatory Situation on Waste at EC and OECD levels, published February 1993.

Accordingly, the present invention relates to a method for upgrading silicon-containing solid residues obtained after leaching of copper from copper-containing residues from direct synthesis of organochlorosilanes, said method being characterized in that the solid residue, optionally together with an oxidation agent, is supplied to a smelting furnace where the residues are melted and form a molten metallic phase substantially containing silicon and a calcium silicate slag and tapping of the molten metallic phase and an inert slag from the smelting furnace.

According to a preferred embodiment the residues are dried and agglomerated before they are supplied to the smelting furnace. The agglomeration is carried out by conventional methods such as for example pelletizing using a suitable binder. Alternatively the residues can be supplied to the smelting furnace in powder form by injection through a hollow electrode or by injection through a lance or through nozzles arranged in the furnace bottom or in the furnace body. When the residues are supplied through a hollow electrode or injected through lances or nozzles directly into the molten bath, the residues can either be in powder form or agglomerated form.

If necessary CaO, $SiO_2$ or $Al_2O_3$ are added as slag forming materials in order to produce a calcium silicate or a calcium aluminate silicate slag which is liquid at the temperature in the smelting furnace and is inert after solidification. The basicity of the slag defined for example as weight ratio $CaO/SiO_2$ is preferably adjusted within the range of 0.5 to 3.0.

The smelting process may be carried out in plasma heated furnaces or in furnaces equipped with graphite- or carbon electrodes. The current supply can be direct current or alternate current. Both open, semi-closed or closed smelting furnaces can be used. The use of a closed smelting furnace gives, however, the best control of gas production. This may be an advantage as to the amount of gas and to avoid outlet of dioxine to the environment.

As the oxidizing agent a metal oxide or an oxygen containing gas can be used. The purpose of the supply of an oxidation agent is to oxidize any elemental carbon present in the residue.

According to a preferred embodiment, an iron oxide source is added as oxidation agent to the smelting furnace in an amount sufficient to oxidize elemental carbon present in the residue. In this case the molten metallic phase will, in addition to silicon and copper, contain iron which during the solidification of the metallic phase will form a $FeSi_2$ intermetallic phase.

During the smelting of the residue some amorphous silica dust will be formed which will follow the off gas from the furnace. This silica dust can be recovered from the off gas in for example a bag house filter and can be used as a binder for producing agglomerates of the residue or it can be used as an additive in the production of concrete and mortar. Alternatively the gas can be cleaned by wet cleaning, whereby the amorphous silica can be recovered in the form of a liquid slurry.

By the method according to the present invention silicon or a silicon-iron alloy is obtained which can be used as an additive in the production of steel or cast iron or as a reduction agent in silicothermic production of metals or metal alloys. The inert slag can be used as a filler material or it can be deposited.

EXAMPLE

A solid residue obtained after leaching of copper from a copper-containing residue for organochlorosynthesis was agglomerated using a binder which, based on the weight of the agglomerates, consisted of 2% by weight of amorphous silica fume, 3% by weight of slaked lime, 2% by weight of an aqueous sugar solution and water in an amount of up to 17% by weight. Agglomerates having a composition as shown in Table 1 were melted in a smelting furnace equipped with a plasma burner.

TABLE 1

Composition of agglomerated solid residue.

| Element | Weight % |
|---|---|
| Fe | 1.7 |
| Zn | 0.01 |
| Cu | 0.3 |
| Mn | 0.03 |
| Cr | 0.01 |
| Ti | 0.13 |
| Ca | 1.2 |
| Al | 0.33 |
| Mg | 0.02 |
| C | 4.8 |
| Cl | 1.13 |
| Si | 78.6 |
| Remainder | Oxygen |

Before the solid residue was supplied to the smelting furnace, a start melt was established in the furnace comprising silicon and a slag consisting of about 55% by weight of CaO and about 45% by weight of $SiO_2$.

The solid residue was together with CaO and $SiO_2$ as slagforming material and $Fe_2O_3$ as oxidation agent supplied to the slag bath. The purpose of the addition of $Fe_2O_3$ was to consume free carbon in the solid residue by reduction of $Fe_2O_3$ to Fe.

From the smelting furnace a silicon-iron alloy and a calcium silicate slag was tapped. The chemical analysis of the produced silicon-iron alloy is shown in Table 2. The silicon-iron alloy can for example be used as an additive in steel and cast iron production or as a reduction agent in silicothermic production of metals and metal alloys.

TABLE 2

Composition of Si—Fe (Cu)-alloy.

| Element | Weight % |
|---|---|
| Al | 0.50 |
| Ca | 1.4 |
| Ti | 0.14 |
| Fe | 9.9 |
| Cu | 0.4 |
| Si | 86.0 |
| $O_2$ | <1.0 |

The off-gas from the smelting furnace was cleaned in a wet cleaning apparatus. From the wet cleaning apparatus a sludge consisting essentially of $SiO_2$ was recovered.

The chemical analysis of the solidified calcium aluminate slag is shown in Table 3. This kind of slag fullfills the requirements set to an inert material stated in Review of Regulatory Situation on Waste at EC and OECD levels, published February 1993.

TABLE 3

Composition of slag.

| | Weight % |
|---|---|
| CaO | 56.4 |
| FeO | 2.9 |
| MgO | <0.01 |
| $TiO_2$ | 0.04 |
| MnO | 0.03 |
| ZnO | 0.011 |
| PbO | <0.01 |
| $SiO_2$ | 39.5 |
| $Al_2O_3$ | 1.2 |

We claim:

1. Method for upgrading a silicon and copper containing solid residue to obtain a silicon product comprising the steps of:

obtaining a solid residue from a direct synthesis of organochlorosilanes, said solid residue being a silicon and copper containing waste product from said synthesis;

leaching said residue to extract copper therefrom;

supplying the solid leached residue optionally together with an oxidation agent to a smelting furnace;

melting the residue and optional oxidizing agent to form a melt comprising a molten metallic phase substantially containing silicon and a slag phase comprising a calcium silicate slag; and tapping the molten metallic phase and said slag phase from the smelting furnace, said slag phase being inert and said molten metallic phase being said silicon product.

2. Method according to claim 1 wherein the residue is dried and agglomerated before the residue is supplied to the furnace.

3. Method according to claim 1 wherein the residue is supplied to the smelting furnace in powder form by injection through a hollow electrode or by injection into the melt by means of a lance or through nozzles arranged in the smelting furnace.

4. Method according to claim 1 wherein at least one slag forming material selected from the group consisting of CaO, $SiO_2$, and $Al_2O_3$ is added to the furnace to produce a liquid slag.

5. Method according to claim 1 wherein said slag has a basicity defined as a weight ratio $CaO/SiO_2$, and said basicity is adjusted within a range of 0.5 to 3.0.

6. Method according to claim 1 wherein said oxidizing agent is a metal oxide or an oxygen-containing gas.

7. Method according to claim 6 wherein said metal oxide is iron oxide.

8. Method according to claim 4 wherein the slag has a basicity defined as a weight ratio $CaO/SiO_2$ and said basicity is adjusted within the range of 0.5 to 3.0.

* * * * *